United States Patent [19]

Lentz et al.

[11] 4,407,298

[45] Oct. 4, 1983

[54] CONNECTOR FOR THERMODILUTION CATHETER

[75] Inventors: David J. Lentz, Mission Viejo; Richard B. Houghton, Irvine, both of Calif.

[73] Assignee: Critikon, Inc., Tampa, Fla.

[21] Appl. No.: 283,716

[22] Filed: Jul. 16, 1981

[51] Int. Cl.³ .............................................. A61B 5/02
[52] U.S. Cl. ..................................... 128/713; 128/691
[58] Field of Search ....................... 128/691, 713, 736; 339/18 R, 18 C, 19, 222

[56] References Cited

U.S. PATENT DOCUMENTS

| | | | |
|---|---|---|---|
| 3,235,830 | 2/1966 | Newton | 339/18 R |
| 3,671,918 | 6/1972 | Mitchell | 339/18 R |
| 3,720,199 | 3/1973 | Rishton et al. | 128/1 D |
| 3,995,623 | 12/1976 | Blake et al. | 128/2.06 E |

OTHER PUBLICATIONS

"The EDSLAB® Thermodilution Catheters": Published by Edwards Laboratories, 6/73.
"Thermodilution Cardiac Output Determination with a Single Flow-Directed Catheter": American Heart Journal 83(3), 306-11, (1972).
"The Swan-Ganz® Flow-Directed Thermodilution Catheter": Published by Edwards Laboratories, Inc., 7/78, pp. 1-8.

Primary Examiner—Kyle L. Howell
Assistant Examiner—Max F. Hindenburg
Attorney, Agent, or Firm—Audley A. Ciamporcero, Jr.

[57] ABSTRACT

A thermodilution catheter assembly for use in determining cardiac output includes a special connector for joining the catheter to the output computer. Catheter size indicator links housed in the connector automatically communicate the size of the catheter to the computer when the connection is made. As an optional feature, the connector additionally includes means to automatically energize the computer when the connection is made.

6 Claims, 5 Drawing Figures

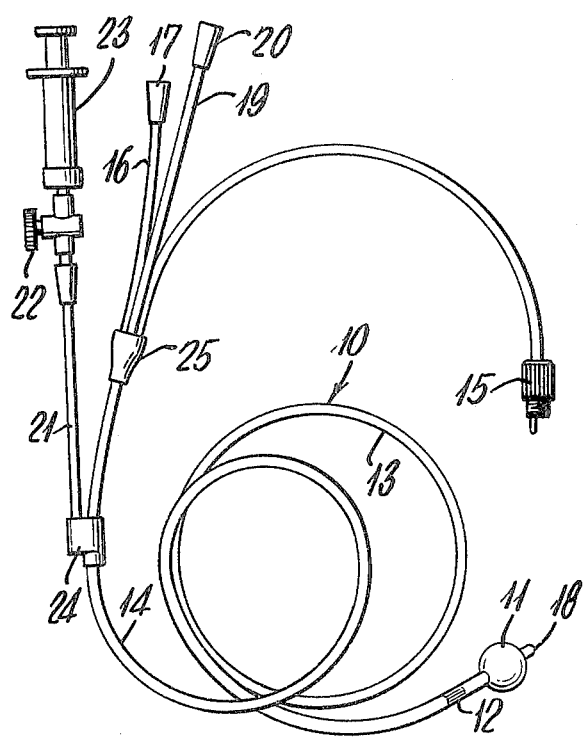
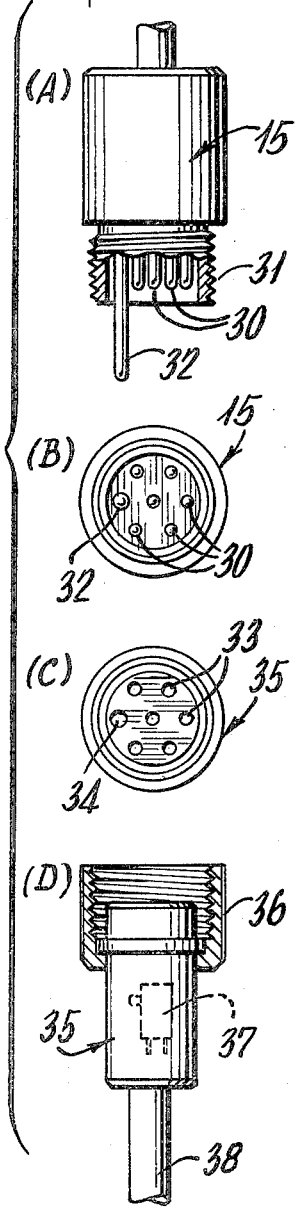
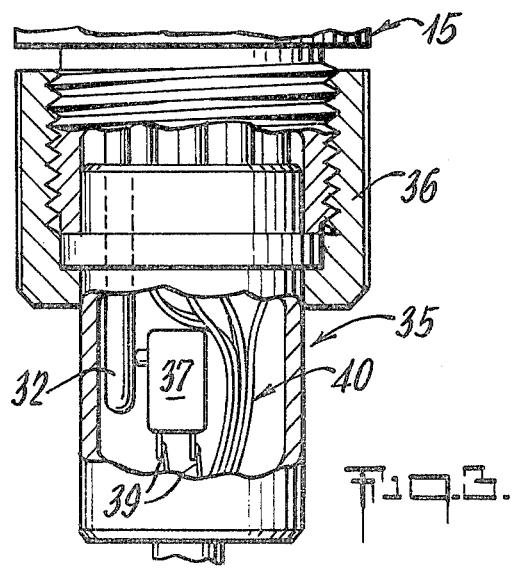

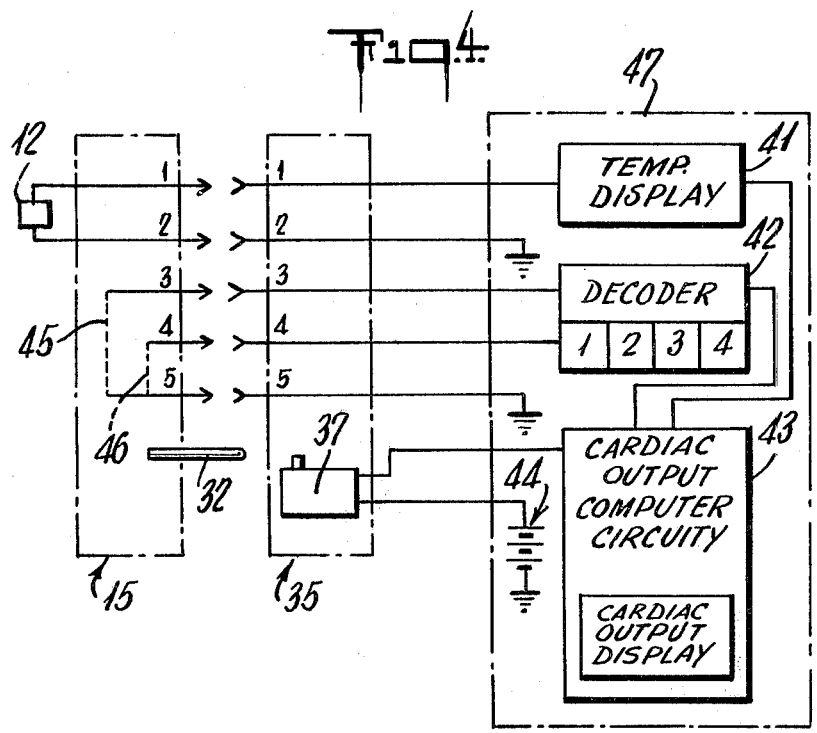
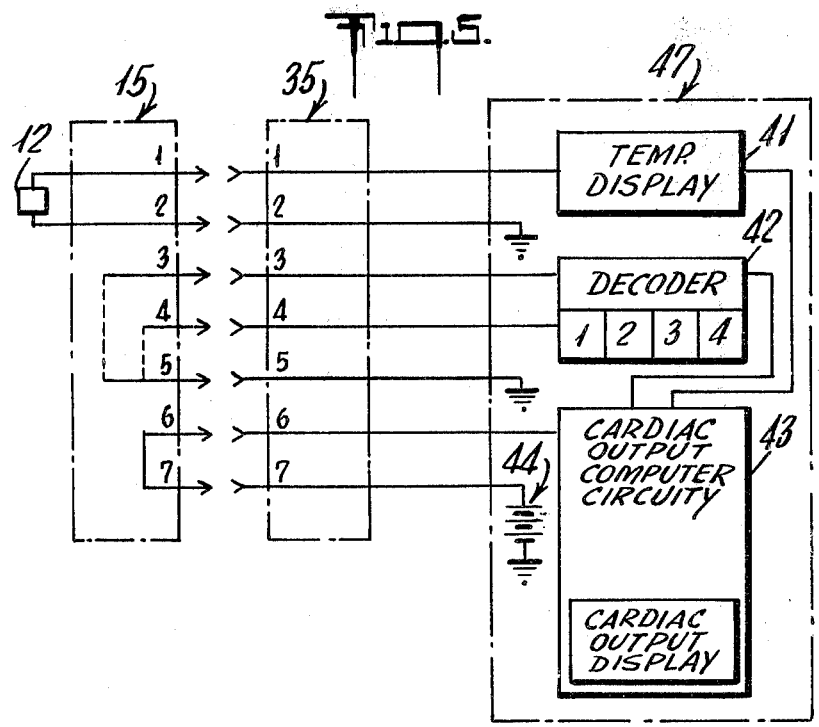

4,407,298

CONNECTOR FOR THERMODILUTION CATHETER

BACKGROUND OF INVENTION

1. Field of the Invention

This invention relates to thermodilution catheter assemblies for determining cardiac output and, more particularly, to the assembly for electrically connecting the catheter to an output computer.

2. Description of Prior Art

The use of thermodilution catheters to determine cardiac output is well-known. The catheters are typically small-diameter balloon catheters equipped with distal temperature sensing means and a lumen opening a short distance proximal to the temperature sensing means for introducing a low temperature liquid injectate into the blood stream. The displacement of temperature resulting from the introduction of the injectate into the blood stream is sensed by the temperature sensing means, and the magnitude and duration of temperature displacement is used to compute the blood flow rate or cardiac output. A representative thermodilution catheter is illustrated in U.S. Pat. No. 3,995,623.

The blood flow rate is computed from the displacement of blood temperature according to the Stewart-Hamilton dilution equation for a thermal indicator as described in U.S. Pat. No. 3,987,788. In accordance with the teachings of this reference, numerical values are manually entered into the system for a computation constant, blood temperature, and injectate temperature. The computation constant is derived from the composition of the injectate, the volume of injectate, and a correction factor for the rise in temperature of the injectate as it passes through the lumen of the catheter to the injectate orifice. The computation constant for any given set of operating conditions is selected from a table provided by the computer manufacturer and is manually entered into the system by the operator.

In the vast majority of cases, the thermodilution technique is carried out with a standard five percent (5%) glucose solution, and a standard injectate volume for a given size catheter. Thus, a single computation constant is used in most cases for any given sized catheter. It is accordingly an object of the present invention to provide a means for automatically entering a standard computation constant for a given size catheter into the computer when the catheter is connected, the computer being provided with manual override means in the event nonstandard thermodilution conditions are employed.

SUMMARY OF THE INVENTION

In accordance with the present invention, the thermodilution catheter is provided with an electrical connector programmed to communicate to the computer the size of the catheter being employed, and to thereby allow the computer to enter a predetermined computation constant for that size catheter. Thermodilution catheters of the present invention are produced in four standard sizes, and are provided with catheter-size indiction means housed within the body of the connector used to join the catheter to the computer. The catheter connector is a multipinned plug assembly including three pins for indicating catheter size according to the presence or absence of an electrically conductive link between two of the pins and a grounded third pin in a standard four-level matrix. A one-of-four decoder in the computer recognizes the signal communicated by the catheter and enters the appropriate preprogrammed computer constant for the indicated catheter size. If a nonstandard volume or composition of injectate is to be used in the procedure, a new computation constant is entered into the computer via the manual override capability.

Catheters of the present invention may also include blood pressure monitoring capability via one or more lumens opening through the wall of the catheter. Right atrial pressure may be monitored through the injectate lumen, the orifice of which is located at a distance from the catheter tip calculated to place the orifice in the right atrium of the heart when the catheter is positioned with the thermistor in the pulmonary artery. Pulmonary artery and pulmonary capillary wedge pressures may be monitored through a second lumen opening in the distal tip of the catheter.

The catheter connector may additionally include computer power actuating means to automatically energize the computer when the catheter is attached. Such power actuating means may comprise a mechanical power-on switch such as a pin extending from the catheter connector and adapted to close an electrical contact in a receiving computer connector socket. Alternatively, the catheter connector may include a power-link, power-on switch comprising two bridged electrically conductive pins adapted to complete an electrical circuit when inserted into the receiving computer connector socket.

DESCRIPTION OF DRAWINGS

FIG. 1 is a view in perspective of a representative thermodilution catheter.

FIG. 2 provides side and end views of the catheter connector plug and receiving computer connector socket.

FIG. 3 is a plan view of the joined catheter and computer connectors with the computer connector socket in partial section to provide an internal view.

FIG. 4 is a schematic representation of the circuitry employed in a connector assembly utilizing a mechanical power-on switch.

FIG. 5 is a schematic representation of the circuitry in a connector assembly utilizing a power-link, power-on switch.

DESCRIPTION

Referring now to FIG. 1, there is illustrated a conventional thermodilution catheter 10 comprising distal tip orifice 18, balloon 11, thermistor 12, and injectate orifice 13. The distal tip orifice communicates through an internal lumen within catheter body 14 to tubular extension 19 terminating in luer fitting 20. The injectate orifice similarly communicates through an internal lumen to tubular extension 16 terminating in luer fitting 17. Balloon 11 communicates through an internal lumen in body 14 to connector 24 and then through tubular extension 21. A syringe 23 with an intermediate stopcock 22 is connected to extension 21 for the purpose of inflating the balloon.

Thermistor 12 is connected by fine wires embedded in the wall of catheter body 14 to individual pins in catheter connector 15. Connector 15 is illustrated in greater detail in FIG. 2(A) where it is seen to include a housing having electrical contact pins 30 enclosed by threaded collar 31 and mechanical switch actuating pin 32 extending beyond collar 31. The pins are suitably spaced within the confines of collar 31 as illustrated in FIG. 2(B).

The corresponding computer connector socket adapted to receive the catheter connector plug is illustrated in FIG. 2(C) and (D). Computer connector 35 includes electrical pin receptors 33, a mechanical switch pin receptor 34, and a threaded slip collar 36 to secure connectors 15 and 35 when connection is made.

Connector 35 further includes an internally mounted, mechanical switch 37 which is actuated by pin 32 when the catheter is connected as illustrated in FIG. 3 FIG. 3 additionally illustrates wires 40 extending from pin receptors 30 to cable 38 leading to the computer.

Three electrical pins of connector 15 are dedicated to catheter size indication links which communicate the size of the catheter to a utilization apparatus, for example the computer. With reference to FIG. 4, the connector assembly is represented in a schematic circuit diagram with electrical contact pins numbered 1 through 5. Pins 1 and 2 of the catheter connector are joined to thermistor 12 and feed a signal into the computer which results in a temperature display at 41, and additionally, is utilized to calculate cardiac output at 43.

Catheter size indicator links 45 and 46 bridge pins 3–5 and/or 4–5 respectively of the catheter connector plug. The presence or absence of the two connector links defines four catheter sizes according to the following four-level matrix.

| Catheter size | Pins 3-5 | Pins 4-5 |
|---|---|---|
| 1 | open | open |
| 2 | open | closed |
| 3 | closed | open |
| 4 | closed | closed |

Pin receptors 3 and 4 on the computer side of the connector are connected to a one-of-four decoder 42 which identifies the catheter size and communicates this information to the computer circuity at 43 for use in calculating cardiac output.

With further reference to FIG. 4, the catheter connector plug additionally includes an optional mechanical actuator pin 32. When the catheter plug is inserted into the computer socket, the actuator pin activates a switch such as that identified generally at 37 in FIG. 4. Activation of the switch completes a circuit from battery 44 which in turn activates the main power source to the computer.

With reference to FIG. 5, the catheter connector plug incorporates the same features as FIG. 4 relative to pins 1 through 5. In this embodiment, however, the mechanical power actuator pin is replaced with a power-on link 47 through pins 6 and 7. Connection of the catheter to the computer completes the circuit through the power-on link and activates the main power source to the computer.

As will be apparent in FIG. 4, pins 2 and 5 are electrically grounded and may accordingly be combined as a single ground pin if desired to provide a 4 pin catheter plug assembly. Similarly, the combination of pins 2 and 5 in the assembly of FIG. 5 would result in a 6 pin catheter assembly. These and other modifications which will be apparent to those skilled in the art and are the functional equivalent of the catheter plug assembly as described herein are accordingly included within the scope of the present invention.

In the preceding Figures, the automatic power-on capability is an optional feature of the connector plug which may be replaced by a conventional, manual power-on switch for the computer. As a further alternative, the power-on switching means may be incorporated at the point where interconnecting cable 38 is detachably connected to the computer by incorporating the computer power-on device in the cable-to-computer plug rather than in the catheter-to-cable plug. The power-on device may be a mechanical switch, a power-on link, or other suitable means to automatically activate the main power source to the computer when the cable is attached to the computer.

The catheter size indicator links in the catheter connector are readily fabricated into the molded plug, are totally reliable, and being simple electrical conductors, are very inexpensive. The catheter size indicator links thus have economical and other advantages over the use of resistors of various values to indicate catheter size as used in certain prior art catheters such as that of U.S. Pat. No. 3,720,199. Quality control procedures are likewise simplified since correct link configuration can be determined by simple conductivity tests between the three pins of the catheter plug.

We claim:

1. In a thermodilution catheter having respective distal and proximate ends, temperature sensing means at said distal end and connector means at said proximate end for attaching said thermodilution catheter to a cardiac output computer, the improvement wherein said connector means comprises a plurality of electrically conductive pins, the first and second of said pins being connected to said temperature sensing means, and the third, fourth, and fifth of said pins being adapted to receive conductive bridging members between said third and fifth pair of pins and between said fourth and fifth pair of pins, said connector further selectively comprising, in correspondence to catheter size, connective bridging members to couple selectively said pins and thereby to indicate catheter size according to the following arrangement:

| Catheter size | Pins 3-5 | Pins 4-5 |
|---|---|---|
| 1 | open | open |
| 2 | open | closed |
| 3 | closed | open |
| 4 | closed | closed. |

2. The catheter of claim 1 wherein said connector means additionally includes mechanical power actuating pin means extending therefrom, said pin means being adapted to close an electrical contact in a receiving connector socket.

3. The catheter of claim 1 wherein said connector means additionally includes two power actuating, electrically conductive and electrically bridged pins, said pins being adapted to complete an electrical circuit in a receiving connector socket.

4. The catheter of claim 1 wherein said second and fifth pins are to an electrical ground.

5. The catheter of claim 4 wherein said second and fifth pins are combined to provide a 4 pin catheter connector.

6. In a thermodilution catheter system employing a catheter of one of "N" predetermined sizes, a connector for coupling said catheter to utilization apparatus and for automatically identifying catheter size to said apparatus, said connector comprising a housing defining plural conductor locations adapted to be coupled to respectively corresponding conductor locations on said utilization apparatus, wherein a select plurality "X" of said locations are allocated catheter size identification function in accordance with the relationship "$2^{x-1}=N$", and wherein said housing carries bridging means selectively to interconnect said X locations in N mutually exclusive patterns in respective correspondence to said N predetermined catheter sizes.

* * * * *